United States Patent [19]

Greene et al.

[11] Patent Number: 5,021,342
[45] Date of Patent: Jun. 4, 1991

[54] **EXPRESSION CDNA CLONES ENCODING ANTIGENS OF *ONCHOCERCA VOLVULUS***

[75] Inventors: Bruce M. Greene, Shaker Heights; Thomas R. Unnasch, South Euclid, both of Ohio

[73] Assignee: University Hospitals of Cleveland, Cleveland, Ohio

[21] Appl. No.: 214,264

[22] Filed: Jun. 30, 1988

[51] Int. Cl.[5] .................. C12P 19/34; C12P 21/06; C12N 15/00; C12N 7/00; C12N 1/22; C07H 15/12; C07K 13/00

[52] U.S. Cl. .................. 435/91; 435/69.1; 435/172.3; 435/252.33; 435/320.1; 536/27; 530/350; 935/18; 935/31; 935/47; 935/58; 935/65; 935/73; 935/81

[58] Field of Search ............ 435/69.1, 71.2, 91, 435/172.3, 252.33, 320, 235; 536/27; 530/350; 935/18, 31, 41, 58, 65, 73, 81

[56] References Cited

PUBLICATIONS

Perler, F. et al., Mol Biochem Parasit, vol. 21, pp. 171–178, (1986).
Erttman, K. D. et al., Nature, vol. 327, pp. 415–417, (1987).
Helfman et al., Proc. Nat'l Acad. Sci., vol. 80, pp. 31–35, (1983).
Maniatis, T. et al., Molecular Cloning, A Laboratory Manual, Cold Spring Harbor Laboratory, CSH, N.Y., (1982), pp. 224–246.
S. S. Chirala, "The Nucleotide Sequence of the Lac Operon and Phage Juction in Lambda GtII", vol. 14, No. 14, 1986, Nucleic Acids Research, IRL Press Limited, Oxford England, p. 5935, Department of Biochemistry, Baylor College of Medicine, Houston, Tex., 77030, U.S.A.
H. Schulz-Key, E. J. Albiez, D. W. Buttner, "Tropenmedizin und Parasitologie", Isolation of Living Adult Onchocerca Volvulus from Nodules, Jahrgang Heft, Dec. 4, 1977, Seite 409–560, pp. 427–430.
Pierre Ambroise-Thomas, "Immunological Diagnosis of Human Filariasis: Present Possibilities, Difficulties and Limitations", Laboratory for Parasitology and Tropical Diseases, Faculty of Medicine, University of Grenoble, La Troche, France, pp. 108–128.
J. L. Ngu, "Immunological Studies on Onchocerciasis", "Varying Skin Hypersensitivity and Leucocyte Migration Inhibition in a Clinical Spectrum of the Disease", University Center for Health Sciences (C.U.S.S.), University of Yaounde, Cameroon, pp. 269–279.
Higashi, Gene I., "Immunodiagnostic Tests for Protozoan and Helminthic Infections", Department of Epidemiology, University of Michigan, School of Public Health, Ann Arbor, 1984 Alan R. Liss, Inc. Diagnostic Immunology 2:2–18 (1984), pp. 1–18.
Betty Kirkwood et al., "Relationships Between Mortality, Visual Acuity and Microfilarial Load the Area of the Onchocerciasis Control Program", Transactions of the Royal Society of Tropical Medicine and Hygiene, vol. 77, No. 6, 862–868 (1983), pp. 826–868.
"Strategic Plan for ONCHOCERCIASIS RESEARCH", Sep. 1985, The Edna McConnell Clark Foundation, 250 Park Ave., Suite 900, New York, N.Y., 10017, U.S.A., Edna McConnell Clark Foundation, Joseph A. Cook, M.D., Director, Mary Jo Mullan, Assistant, Joan M. Jacobs, Secretary, pp. 1–11.

(List continued on next page.)

*Primary Examiner*—Robin L. Teskin
*Assistant Examiner*—Joan Ellis
*Attorney, Agent, or Firm*—Sprung Horn Kramer & Woods

[57] ABSTRACT

A cDNA clone (λRAL-1) that encodes a protein with an apparent molecular weight of 42,000 *in vivo* and which clone binds with *O. volvulus* antisera.

A recombinant antigen produced by the aforementioned clone, which antigen stimulates T cells from infected individuals to proliferate.

A DNA which codes for an *O. volvulus* peptide sequence, the sequence containing three repeats of the polypeptide sequence KKPEDWD.

8 Claims, 8 Drawing Sheets

OTHER PUBLICATIONS

C. D. Mackenzie, J. F. Williams, B. M. Sisley, M. W. Steward, and J. O'Day, "Variations in Host Responses and the Pathogenesis of Human Onchocerciasis", Reviews of Infectious Diseases, vol. 7, No. 6, Nov.-Dec., 1985, by the University of Chicago, pp. 802–808.

Ming M. Wong, et al., "Dirofilaria Immitis: Fate and Immunogenicity of Irradiated Infective Stage Larvae in Beagles", *Experimental Parasitology* 35, 465–474 (1974), Sep. 24, 1973, California Primate Research Center, and Departments of Physiological Sciences and Veterinary Microbiology, pp. 465–474.

W. J. Konzek, H. Figueroa Marroquin, "Attempts to Establish Onchocerca Volvulus Infection in Primates and Small Laboratory Animals", Acta Tropica 39, 317–324 (1982), Correspondence: Dr. W. J. Kozek, Cideim, Apartado Aereo 5390, Calif., Columbia, S.A.

John B. Dame, Jackie L. Williams, et al., "Structure of the Gene Encoding the Immunodominant Surface Antigen on the Sporozoite of the Human Malaria Parasite Falciparum", Research Article, pp. 593–599.

Sadao Nogami, et al., "Antigenic Similarity of Onchocerca Volvulus to Other Helminths Examined by Monoclonal Antibodies Against O. Volvulus", Japan, J. Exp. Med. vol. 56, 4, pp. 177–183, Department of Parasitology, Institute of Medical Science, University of Tokyo, Minato-ku, Tokyo 108.

Jay A. Berzofsky, "Intrinsic and Extrinsic Factors in Protein Antigenic Structure", pp. 932–940, Science, vol. 229.

Jeffrey V. Ravetech, Jarema Kochan, Margaret Perkins, SCIENCE, vol. 227, Dec. 4, 1984, accepted Jan. 16, 1985, "Isolation of the Gene for a Glycophorin-Binding Protein Implicated in Erythrocyte Invasion by a Malaria Parasite", Mar. 29, 1985, pp. 1593–1597.

Libuse Bobek, et al., "Characterization of a Female-Specific cDNA Derived from a Developmentally Regulated mRNA in the Human Blood Fluke Schistosoma Mansoni", Proc. Natl. Acad. Sci. U.S.A., vol. 83, pp. 5544–5548, Aug. 1986, Developmental Biology.

William E. Collins et al., "Immunization of Aotus Monkeys with Recombinant Proteins of an Erythrocyte Surface Antigen of Plasmodium Falsiparum", *Nature*, vol. 323, Sep. 18, 1986, pp. 259–262.

Jon A. Yates and Gene I. Higashi, "Brugia Malayi: Vaccination of Jirds with Cobalt-Attenuated Infective Stage Larvae Protects Against Homologous Challenge", Am. J. Trop. Med. Hyg., 34(6), 1985, pp. 1132–1137, Accepted Jun. 25, 1985.

W. Ripley Ballou et al., "Immunogenicity of Synthetic Peptides from Circumsporozoite Protein of Plasmodium Falciparum", *Science*, vol. 228, Feb. 8, 1985; accepted Mar. 21, 1985, pp. 996–999, May 24, 1985.

Renu B. Lal, Thomas J. Lynch and Thomas B. Nutman, "Brugia Malayi Antigens Associated with Lymphocyte Activation in Filariasis", vol. 139, pp. 1652–1657, No. 5, Sep. 1.

B. M. Greene, M. M. Fanning & J. J. Ellner, "Non-Specific Suppression of Antigen-Induced Lymphocyte Blastogenesis in Onchocerca Volvulus Infection in Man", Clin. Exp. Immuno. (1983), 52, 259–265.

John J. Donnelly, Ph.D.; et al., "Ocular Immunopathologic Findings of Experimental Onchocerciasis", Arch Ophthaimol, vol. 102, Apr. 1984, pp. 628–634.

John J. Donnelly et al., "Experimental Ocular Onchocerciasis in Cynomolgus Monkeys", vol. 27, pp. 492–499.

Bruce M. Greene, "Primate Model for Onchocerciasis Research", Division of Geographic Medicine, Department of Medicine, Case Western Reserve University School of Medicine, University Hospitals, Cleveland, Oh. 44106, U.S.A., pp. 236–243.

Vladimir Glisin, Radomir Crkvenjakov, and Craig Byus, "Ribonucleic Acid Isolated by Cesium Chloride Centrifugation", Biochemistry, vol. 13, No. 12, 1974, pp. 2633–2637.

Jyotsna S. Shah, Marc Karam, Willy F. Piessens, and Dyann F. Wirth, "Characterization of an Onchocerca-Specific DNA Clone from Onchocerca Volvulus", Am. J. Trop. Med. Hyg. 37(2), 1987, pp. 376–384.

U. K. Laemmli, "Cleavage of Structural Proteins During the Assembly of the Head of Bacteriophage T4", *Nature*, vol. 227, Aug. 15, 1970, pp. 680–685.

Ueli Gubler and Beth J. Hoffman, "A Simple and Very Efficient Method for Generating cDNA Libraries", Department of Molecular Genetics, Roche Research Center, Hoffmann-La Roche Inc., Gene 25 (1983), 263–269.

Sequences", Proc. Natl. Acad. Sci. U.S.A., vol. 78, No. 6, pp. 3824–3828, Jun. 1981 Immunology.

Marvin Wickens and Pauline Stephenson, "Role of the Conserved AAUAAA Sequence: Four AAUAAA Point Mutants Prevent Messenger RNA 3' End Formation", Research Article, Nov. 30, 1984, pp. 1045–1051.

P. J. Ham, A. J. Banya, "The Effect of Experimental Onchocerca Infections on the Fecundity and Oviposition of Laboratory Reared Simulium sp. (Diptera, Simuliidae)", Tropenmed. Parasit. 35 (1984), pp. 61–66.

Bert Vogelstein and David Gillespie, "Preparative and Analytical Purification of DNA from Agarose", Proc. Natl. Acad. Sci., U.S.A., vol. 76, No. 2, pp. 615–619, Feb. 1979, Biochemistry.

Peter H. Schreier et al., "A Fast and Simple Method for Sequencing DNA Cloned in the Single-Stranded Bacteriophage M13", J. Mol. Biol. (1979), 129, 169–172.

F. Sanger, S. Nicklen, and A. R. Coulson, "DNA Sequencing with Chain-Terminating Inhibitors", Proc. Natl. Acad. Sci. U.S.A., vol. 74, No. 12, pp. 5463–5467, Dec. 1977, Biochemistry.

Harry Towbin, Theophil Staehelin, and Julian Gordon, "Electrophoretic Transfer of Proteins from Polyacrylamide Gels to Nitrocellulose Sheets: Procedure and Some Applications", Proc. Natl. Acad. Sci. U.S.A., vol. 76, No. 9, pp. 4350–4354, Sept. 1979, Biochemistry.

E. M. Southern, "Detection of Specific Sequences Among DNA Fragments Separated by Gel Electrophoresis", J. Mol. Biol. (1975), 98, 503–517.

Thomas P. Hopp and Kenneth R. Woods, "Prediction of Protein Antigenic Determinants from Amino Acid

| kb | A | O | H |
|---|---|---|---|
| 4.3 — | | | |
| 2.3 — | | | |
| 2.0 — | | | |
| 1.9 — | | | |
| 1.1 — | | | |
| 0.9 — | | | |
| 0.6 — | | | |
| 0.4 — | | | |

```
         10        20        30        40        50        60
TTTTATGGCGATGCTGTGAAAGATAAAGGTCTCAAGACAACACAGGATGCGAAATTTTAT
PheTyrGlyAspAlaValLysAspLysGlyLeuLysThrThrGlnAspAlaLysPheTyr
         70        80        90       100       110       120
TCGATCGGTGCGAAATTTGATAAGAGTTTTTCAAACAAGGGTAAATCGCTGGTTATCCAA
SerIleGlyAlaLysPheAspLysSerPheSerAsnLysGlyLysSerLeuValIleGln
        130       140       150       160       170       180
TTTAGCGTCAAGCATGAACAGGACATTGATTGTGGCGGTGGCTATGTTAAGCTAATGGCA
PheSerValLysHisGluGlnAspIleAspCysGlyGlyGlyTyrValLysLeuMetAla
        190       200       210       220       230       240
TCGGATGTAAACCTAGAAGATTCCCATGGTGAAACTCCTTATCATATCATGTTCGGTCCT
SerAspValAsnLeuGluAspSerHisGlyGluThrProTyrHisIleMetPheGlyPro
        250       260       270       280       290       300
GACATCTGTGGACCTGGAACAAAGAAAGTCCATGTCATATTCCATTATAAGGACAGGAAT
AspIleCysGlyProGlyThrLysLysValHisValIlePheHisTyrLysAspArgAsn
        310       320       330       340       350       360
CATATGATCAAGAAAGACATTCGGTGCAAGGATGATGTCTTCACTCATCTCTACACTTTG
HisMetIleLysLysAspIleArgCysLysAspAspValPheThrHisLeuTyrThrLeu
        370       380       390       400       410       420
ATTGTAAACTCTGACAACACCTATGAAGTTCAAATTGACGGTGAAAAGGCTGAATCTGGT
IleValAsnSerAspAsnThrTyrGluValGlnIleAspGlyGluLysAlaGluSerGly
        430       440       450       460       470       480
GAGCTGGAAGCAGATTGGGACTTCCTTCCTCCAAAGAAAATTAAGGATCCAGATGCAAAA
GluLeuGluAlaAspTrpAspPheLeuProProLysLysIleLysAspProAspAlaLys
        490       500       510       520       530       540
AAACCAGAAGACTGGGACGAGCGAGAATTTATCGATGATGAGGATGATAAGAAACCCGAA
LysProGluAspTrpAspGluArgGluPheIleAspAspGluAspAspLysLysProGlu
        550       560       570       580       590       600
GATTGGGACAAGCCGGAACACATTCCTGATCCTGATGCTAAGAAACCGGAGGACTGGGAT
AspTrpAspLysProGluHisIleProAspProAspAlaLysLysProGluAspTrpAsp
```

```
                610        620        630        640        650        660
GATGAAATGGATGGGGAATGGGAGCCACCGATGGTTGATAATCCTGAATATAAAGGAGAG
AspGluMetAspGlyGluTrpGluProProMetValAspAsnProGluTyrLysGlyGlu 670        680        690        700        710        720
TGGAAGCCGAAACAAAAGAAAAATCCTGCATACAAGGGCAAATGGATCCATCCAGAAATC
TrpLysProLysGlnLysLysAsnProAlaTyrLysGlyLysTrpIleHisProGluIle 730        740        750        760        770        780
GAAATTCCAGATTATACTCCAGACGATAATTTGTATGTTTATGATGATATTGGAGCAATT
GluIleProAspTyrThrProAspAspAsnLeuTyrValTyrAspAspIleGlyAlaIle 790        800        810        820        830        840
GGCTTTGATTTGTGGCAAGTAAAATCAGGAACCATTTTTGATGACGTCATTGTGACAGAT
GlyPheAspLeuTrpGlnValLysSerGlyThrIlePheAspAspValIleValThrAsp 850        860        870        880        890        900
AGTGTGGAGGAGGCCAAGAAGTTTGGTGAAAAGACATTGAAAATAACGAGGGAAGGTGAA
SerValGluGluAlaLysLysPheGlyGluLysThrLeuLysIleThrArgGluGlyGlu 910        920        930        940        950        960
AAGAAAAAGGGAAAAAAAACAAAAAAACAGAAGAAGAAAGAGAAGAATGAAAAGATCAAA
LysLysLysGlyLysLysThrLysLysGlnLysLysLysGluLysAsnGluLysIleLys 970        980        990       1000       1010       1020
AAGGAAAAAATGAAAAAAGGAAAAGAGCAAACAGAAAAAAAAAAAGTAAGGAACGTCA
LysGluLysMetLysLysArgLysArgAlaAsnArgLysLysLysLysEnd 1030       1040       1050       1060       1070
AAGGGAAAACAAAAAATAAAAAAAATAAAATTCAAAGAGAAAAGAAAAAAAAAAAA
```

FIG. 7B-2

EXPRESSION CDNA CLONES ENCODING ANTIGENS OF *ONCHOCERCA VOLVULUS*

BACKGROUND OF THE INVENTION

1. Field of the Invention

The present invention concerns a cDNA clone (λRAL-1) which encodes a protein with an apparent molecular weight of 42,000 in vivo and which clone reacts strongly with *O. volvulus* antisera. The invention also relates to a recombinant antigen produced by this clone, which stimulates T cells from infected individuals to proliferate. Still further, the invention is directed to an *O. volvulus* peptide sequence which contains three repeats of polypeptide sequence KKPEDWD.

2. Background Information

Onchocerciasis, or river blindness, is a major cause of infectious blindness in the world. In severely affected areas, as many as half of the adult males may be blinded by the disease (World Health Organization, Edpidemology of Onchocerciasis, WHO Tech. Rep. Ser. 597.: 1-99, (1976)), and mortality rates in such persons are increased as much as four fold (B. Kirkwood, P. Smith, T. Marshall and A. Prost, "Relationships Between Mortality, Visual Acuity and Microfilarial Load in the Area of the Onchocerciasis Control Program", *Trans. Roy. Soc. Trop. Med. Hyg.*, 77: 862-863, (1983)). Attempts to control the disease have centered on control of the vector for the parasite, the blackfly Simulium sp., as well as on the development of chemotherapeutic agents which may be used to eliminate the parasite from infected individuals. Unfortunately, control of the vector has proven extremely difficult. Furthermore, to date no practical chemotherapeutic agent has been identified which kills the adult form of the parasite.

Because neither vector control nor chemotherapy has proven successful in controlling the disease, the development of a vaccine against infection with the parasite has become a high priority (Strategic Plan for Onchocerciasis Research, Edna McConnell Clark Foundation, N.Y., N.Y., (1985)). In order to develop a vaccine, it is necessary to first identify antigens which induce immunity against the parasite. In the case of onchocerciasis, however, the identification of such antigens is complicated by the fact that much of the pathology seen during the course of the disease may be caused by the induction of the immune response of the host to certain antigens of the parasite (C. D. MacKenzie, J. F. Williams, B. M. Sisley, M. W. Steward and J. O'Day, "Variations in Host Responses and the Pathogenesis in Human Onchocerciasis", *Rev. Info Dis.*, 7: 802-808, (1985)). Because of this concern, it is necessary to delineate as fully as possible which parasite antigens are involved in inducing potentially beneficial, as opposed to harmful aspects of the host immune response.

In order to undertake such a dissection of the immune response, large quantities of purified parasite antigens are required. However, no animal host has been identified which can be used to provide the various stages of *O. volvulus* in quantity. As a consequence, the lack of parasite material has posed a major impediment to immunological studies. This problem has been particularly acute for the study of the infectious form of the parasite, the third stage larva, or L3. This is due to the fact that the infective larvae must be obtained by dissection of infected blackflies, which are extremely difficult to obtain. Antigens from this third stage larva may be especially important, since it has been shown in other filarial infections that irradiated infective larvae can induce protective immunity (M. M. Wong, M. F. Guest and M. J. Laviopierre, "*Dirofilaria immitis:* Fate and Immunogenicity of Irradiated Infective Stage Larvae in Beagles", *Exp. Parasitol.*, 35: 465-474, (1974); J. A. Yates, and G. I. Higashi, "*Brugia malayi:* Vaccination of Jirds with $^{60}$Cobalt-Attenuated Infective Stage Larvae Protects Against Homologous Challenge", *Am. J. Trop. Med. Hyg.*, 34: 1132-1137 (1985)).

DEFINITIONS

Genbank: NIH Genetic Sequence Data Bank
BNRF: National Biomedical Research Foundation Protein Data Bank

Amino Acid Abbreviations

| Amino Acid | Three Letter Abbreviation | One Letter Abbreviation |
|---|---|---|
| aspartic acid | Asp | D |
| asparagine | Asn | N |
| threonine | Thr | T |
| serine | Ser | S |
| glutamic acid | Glu | E |
| glutamine | Gln | Q |
| proline | Pro | P |
| glycine | Gly | G |
| alanine | Ala | A |
| cysteine | Cys | C |
| valine | Val | V |
| methionine | Met | M |
| isoleucine | Ile | I |
| leucine | Leu | L |
| tyrosine | Tyr | Y |
| phenylalanine | Phe | F |
| lysine | Lys | K |
| histidine | His | H |
| arginine | Arg | R |

Nucleic Acid Abbreviations

| | |
|---|---|
| T | thymidine |
| A | adenine |
| G | guanine |
| C | cytosine |
| U | uracil |

Nucleotide - A monomeric unit of DNA or RNA containing a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C and uracil ("U").

DNA Sequence - A linear array of nucleotides connected one to the other by phosphodiester bonds between 3' and 5' carbons of adjacent pentoses.

Codon - A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

Reading Frame - The grouping of codons during translation of mRNA into amino acid sequences. During translation, the proper reading frame must be maintained. For example, the sequence GCTGGTTGTAAG may be translated in three reading frame or phases, each of which affords a different amino acid sequence GCT GGT TGT AAG AAG - Ala-Gly-Cys-Lys
G CTG GTT GTA AG - Leu-Val-Val
GC TGG TTG TAA G - Trp-Leu-(STOP).

Polypeptide - A linear array of amino acids connected one to the other by peptide bonds between the alpha-amino and carboxy groups of adjacent amino acids.

Genome - The entire DNA of a cell or a virus. It includes inter alia the structural genes coding for the polypeptides of the cell or virus, as well as its operator, promotor and ribosome binding and interaction sequences, including sequences such as the Shine-Dalgarno sequences.

Structural Gene - A DNA sequence which encodes through its template or messenger RNA ("mRNA") a sequence of amino acids characteristic of a specific polypeptide.

Transcription - The process of producing mRNA from a structural gene.

Translation - The process of producing a polypeptide from mRNA.

Expression - The process undergone by a structural gene to produce a polypeptide. It is a combination of transcription and translation.

Plasmid - A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Bacteriophage - Bacterial virus, many of which consist of DNA sequences encapsulated in a protein envelope or coat ("capsid protein").

Cloning Vehicle - A plasmid, phage DNA or other DNA sequence which is capable of replicating in a host cell, which is characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance. A cloning vehicle is often called a vector.

Cloning - The process of obtaining a population of organisms or DNA sequences derived from one such organism or sequence by asexual reproduction.

Recombinant DNA Molecule or Hybrid DNA - A molecular consisting of segments of DNA from different genomes which have been joined end-to-end outside of living cells and have a capacity to infect some host cell and be maintained therein.

Expression Control Sequence - A sequence of nucleotides that controls and regulates expression of structural genes when operatively linked to those genes. They include the lac system, the trp system, major operator and promoter regions of phage λ, the control region of fd coat protein and other sequences known to control the expression of genes of prokaryotic or eukaryotic cells of their viruses.

Transformation/Transfection - DNA or RNA is introduced into cells to allow gene expression.

"Infected" refers to the introduction of RNA or DNA by a viral vector into the host.

"Injected" refers to the microinjection (use of a small syringe) of DNA into a cell.

SUMMARY OF THE INVENTION

To circumvent the problem of lack of parasite material, an alternative strategy was undertaken rather than to simply isolate antigens directly from the limited amounts of parasite material that are available. This was based upon the identification of cDNA clones that express antigens associated with *O. volvulus* infective larvae. To identify such clones, antisera produced by introducing living effective larvae was introduced into a non-permissive host to screen an *O. volvulus* expression cDNA library. Using this approach, six closes were identified. One clone, designated λ(RAL-1 (clone λRAL-1 was deposited with the American Type Culture Collection(ATCC) on June 28, 1988 and was given deposit No. ATCC 67737), was a member of the class that appeared to react most strongly with the immune sera. Based upon immunoaffinity purified antibody probing of crude *O. volvulus* protein extracts, the mRNA that gave rise to λRAL-1 encoded a protein with an apparent molecular weight of 42,000 in vivo. The recombinant antigen produced by this clone stimulated T cells from infected individuals to proliferate, suggesting that the native antigen related to λRAL-1 has relevance in natural infections. Sequence analysis of the cDNA insert of λRAL-1 revealed the presence of a single long open reading frame, which encoded three repeats of the polypeptide sequence KKPEDWD. The isolation and characterization of λRAL-1 demonstrates that it will be possible to use clones expressing antigens found in *O. volvulus* infective larvae to examine the role that such antigens may play in the development of a protective immune response against the parasite.

The present invention thus resides in a cDNA clone, identified as λRAL-1, that encodes a protein with an apparent molecular weight of 42,000 in vivo and which clone reacts (binds) strongly with *O. volvulus* antisera. The invention further relates to a recombinant antigen produced by this clone which stimulates T cells from infected individuals to proliferate. Still further, the invention concerns a DNA which codes for an *O. volvulus* peptide sequence, which peptide contains three repeats of the polypeptide sequence KKPEDWD.

Figure 7A:
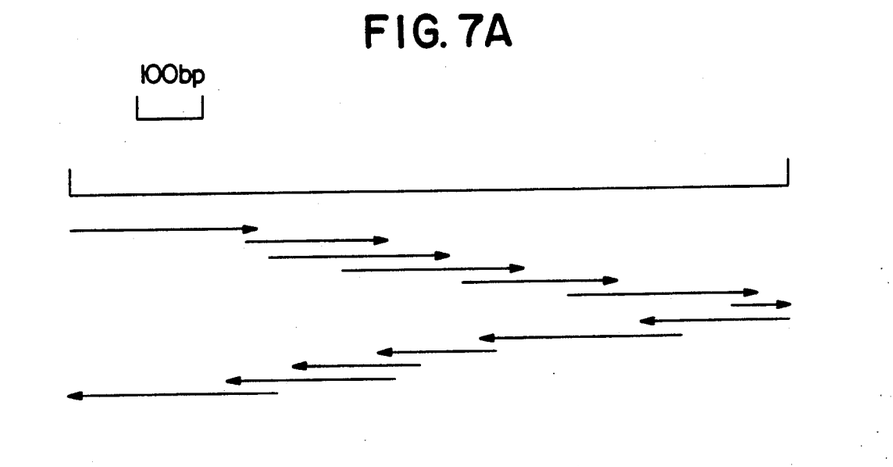
FIGS. 7A-7B are the DNA sequence of the insertod DNA of λRAL-1.
Figure 7B:
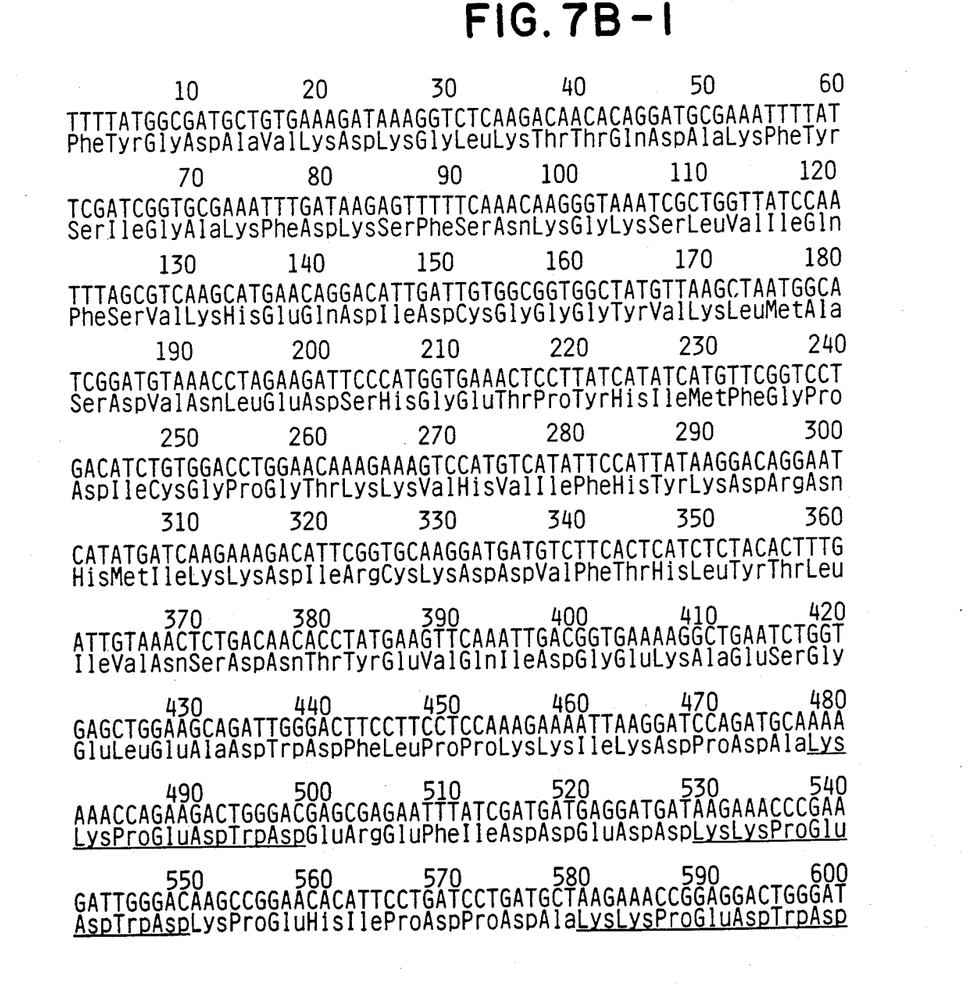
Figure 7B:
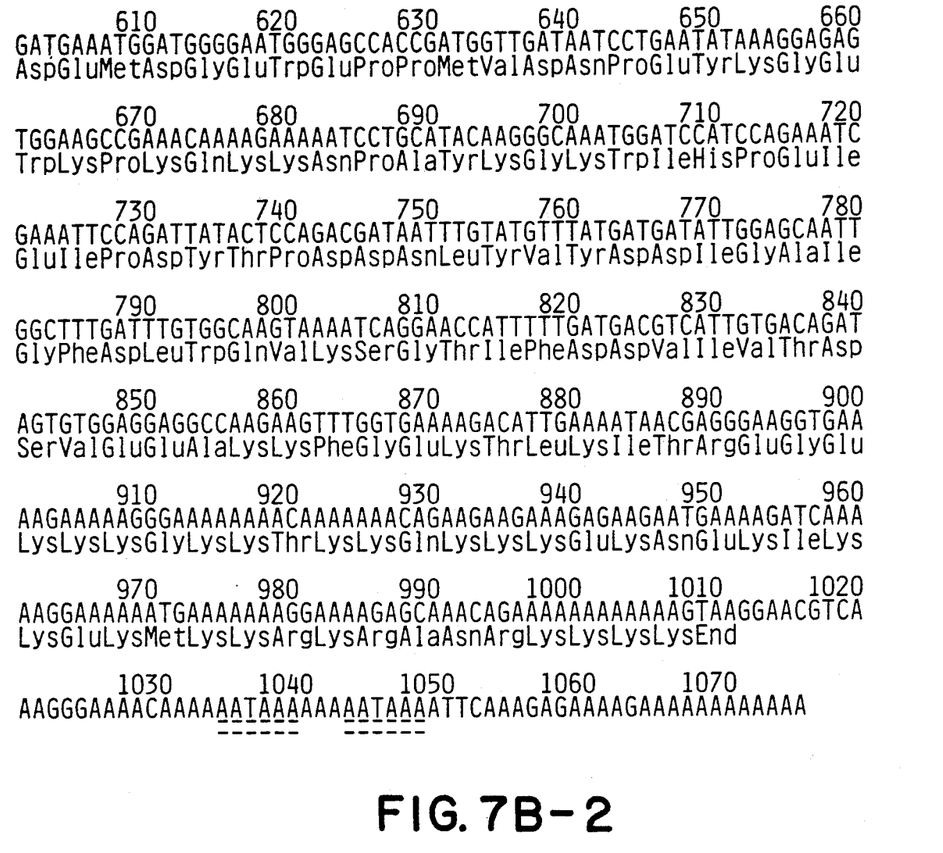

The invention is also directed to a nucleic acid, e.g., a DNA having the sequence shown in FIG. 7, and functional equivalents thereof and fragments thereof.

Still further, the invention relates to a recombinant cloning vehicle having an insert comprising the aforementioned nucleic acid, e.g., DNA.

The present invention further concerns a cell line that is transfected, infected or injected with a replicate recombinant cloning vehicle as described above.

The invention is further directed to a polypeptide having an amino acid sequence corresponding to the entire amino acid sequence or a portion thereof having no less than five amino acids of the sequence shown in FIG. 7.

BRIEF DESCRIPTION OF THE DRAWINGS

The set of lanes labelled "D" are the immunoprecipitated in vitro translation products of *D. immitis* RNA, while the set of lanes labelled "0" are the immunoprecipitated in vitro translation products of *O. volvulus* RNA. In each of the two sets of lanes, N=precipitation with preimmune rabbit serum, A=precipitation with rabbit antiserum raised against adult *O. volvulus,* and L=precipitation with rabbit antiserum raised against *O. volvulus* L3s.

Panel N=filter exposed to preimmune rabbit serum; Panel A-filter exposed to rabbit antiserum raised against adult *O. volvulus,* and Panel L=filter exposed to rabbit antiserum raised against *O. volvulus* L3s. In each panel, Row A=the vector bacteriophage λgt11; Row B=clone λRAA-1, which was isolated with the anti-adult *O. volvulus* antiserum Rows C and D=two independent isolates of the class of clones that are related to λRAL-1 by hybridization analysis, and Row E=an example of an immunoreactive clone which is unrelated to λRAL-1 by hybridization analysis.

Lane A=λRAL-1 insert cloned into pUC 13 in the plus orientation, and Lane B=λRAL-1 cloned into pUC 13 in the minus orientation.

Panel G-antibodies eluted from the column containing immobilized λgt11 proteins, and Panel L=antibodies eluted from the column containing immobilized λRAL-1 proteins.

The set of lanes labelled "1" includes the DNA samples digested with HindIII, and the set labelled "2" includes the samples digested with EcoR1. In each set, H=human DNA and O=*O. volvulus* DNA.

Panel A represents the start point and extent of the sequence obtained from deleted subclones. The complete sequence of the inserted cDNA from λRAL-1 is presented in Panel B, along with the predicted amino acid sequence encoded by the long open reading frame discussed herein. The repeated polypeptide sequence discussed herein is highlighted by the solid underlining, while the consensus poly A addition signals are highlighted by dotted underlining.

DETAILED DESCRIPTION OF THE INVENTION

It is now been found that it is possible to isolate clones which express antigens of *O. volvulus* infective larvae from an expression cDNA library prepared from adult mRNA. Because the library was prepared from the adult form of the parasite, all of the clones isolated to date produce antigens which are recognized by antisera raised against the adult, as well as the larval form of the parasite. It is likely that any additional clones isolated using these reagents will also be recognized by the adult antiserum, although it is possible that some clones isolated in this way may be expressed at different levels in adults expressed in these two stages of the parasite's lifecycle, whether or not they may be expressed in other stages of the life cycle, such as microfilariae, cannot be predicted based on present knowledge.

Since living larvae were used in the immunization protocol described herein, it is possible that some of the antigens recognized by the anti-larval antiserum may in fact be expressed by parasites that had undergone limited development in the rabbit. However, it is known that rabbits do not permit development of the parasite to the adult stage (W. J. Kozek and H. F. Marroquin, "Attempts to Establish *Onchocerca volvulus* Infection in Primates and Small Laboratory Animals", *Acta. Trop.,* 39:317-314, (1982)). In addition, a post-mortem examination of the innoculated rabbit (described hereinbelow) eight weeks following the last injection with infective larvae demonstrated that no parasites were present. This suggests that any development of the parasite past the larval stage must have been very limited in nature.

The clones which have been isolated appear to fall into two classes, based on cross hybridization analysis, suggesting that the clones in these two classes are derived front two different mRNA species. It should be possible to identify clones derived from several additional messages, since the larval antiserum is able to precipitate six distinct polypeptides from the products of in vitro translation of adult RNA.

A representative from the more immunoreactive class of clones has been characterized. This clone, designated λRAL-1, contains an insert of 1076 base pairs (bp). Of these 1076 bp, 1008 bp are contained in a single large open reading frame, which is also in frame with the open reading frame of the beta-galactosidase gene found in pUC 13. Together, the combined open reading frames of the beta-galactosidase moiety 5' to the EcoR1 site of pUC 13 and the open reading frame of the inserted cDNA predict that this system will produce a fusion protein with a predicted size of 41,454. This is in good agreement with the 38,000 polypeptide recognized by the adult antiserum in lysates of cultures of *E. coli* that contain the inserted DNA of λRAL-1 subcloned into pUC 13. This large open reading frame is not in frame with the beta-galactosidase gene of λgt11, however. Although the initial bacteriophage isolate reacts reproducably with both the antiadult and anti-larval antisera, analysis of induced lysates of this clone using Western blots suggested that a stable fusion product was not being produced. All of these results, when taken together, suggest that the synthesis of the recombinant antigen in the original phage isolate is not under the control of the beta-galactosidase gene of λgt11. This phenomenon has been noted previously (J. B. Dame, J. L. Williams, T. F. McCutchan, J. L. Weber, R. A. Wirtz, W. T. Hockmeyer, W. L. Maloy, J. D. Haynes, I. Schneider, D. Roberts, G. S. Sanders, E. P. Reddy, C. L. Diggs and L. H. Miller, "Structure of the Gene Encoding the Immunodominant Surface Antigen on the Sporozoite of the Human Malaria Parasite *Plasmodium falciparum*", Science, 225:593-599, (1984)), and may have been explained by the presence of a fortuitous *E. coli* promoter in the arm of λgt11 (S. S. Chirala, "The Nucleotide Sequence of the Lac Operon and Phage Junction in Lambda gt11", *Nuc. Acids. Res.,* 14:5935, (1986)).

The inserted DNA of λRAL-1 hybridizes to a single message of 1450 bases the adult *O. volvulus* mRNA. The insert of λRAL-1 is 1076bp in length and does not appear to contain an initiating methionine codon. Thus, it is clear that λRAL-1 is not a full length cDNA clone. Since the sequence contains a single long open reading frame that extends through the presumptive 5' end of the insert, it is likely that a portion of the coding region found in the native message is missing in λRAL-1. Exactly how much is missing is difficult to predict, since the length of the poly A tail on the native message is not known. However, antibodies which specifically bind to protein prepared from induced cultures of λRAL-1 lysogens recognize a single polypeptide with a molecular weight of 42,000 in extracts of adult worms. Analysis of the long open reading frame encoded by λRAL-1 suggests that it encodes polypeptide of with a molecular weight of 39,130. If the native antigen is not subjected to post-translational processing, this suggests that λRAL-1 does contain most of the protein coding sequence found in the native message. More importantly, results using the anti-larval antisera described herein clearly demonstrate that the recombinant protein produced by λRAL-1 contains epitopes found in infective larvae. Furthermore, lysates of λRAL-1 specifically stimulate a cellular immune response, demonstrating that the epitopes which it encodes have relevance in a natural infection.

A weak hybridization signal was detected when the insert of λRAL-1 was used to probe Northern blots of *A. suum* RNA. This suggests that a message related to the one that gave rise to λRAL-1 is found in *A. suum*. Results from many previous studies have shown that most of the antigens of different nematode species are not species specific (P. Ambroise-Thomas, "Immunological Diagnosis of Human Filariasis: Present Possibilities, Difficulties and Limitations", *Acta Tropica*, 38: 108–128, (1974); G. I. Higashi, "Immunodiagnostic Tests for Protozoan and Helminthic Infections", *Diagnos. Immunol.*, 2:2–18, (1984)).

Recent studies of antigenic cross reactivity of different parasitic nematodes have suggested that A. *summ-* may be the most closely related species to *O. volvulus* by this criterion (S. Nogami, Y. Hayashi, M. Tanaka, M. Korenaga, I. Tada and H. Tanaka, "Antigenic Similarity of *Onchocerca volvulus* to Other Helminths Examiner by Monoclonal Antibodies against *O. volvulus*", *Jpn. J. Exp. Med.*, 56:177–183, (1986)).

A more complete characterization of any such related antigen in *A. suum* will require antisera specific for the recombinant protein produced by λRAL-1.

The fact that two different restriction enzymes produce a single band when a digest of genomic *O. volvulus* DNA is probed with the purified insert from λRAL-1 suggests that the organization of the gene which encodes λRAL-1 is not complex. In particular, the results suggest that there is only one copy of the gene encoding λRAL-1 in the genome, and that this copy does not contain any extended introns. Although this is the simplest interpretation, other possibilities, such as the presence of a tandem array of repeated genes homologous to λRAL-1 are also possible. The isolation and characterization of genomic clones homologous to the insert of λRAL-1 should provide a definitive answer to this question.

One striking characteristic of the polypeptide encoded by the long open reading frame of λRAL-1 is the fact that it contains three repeats of the sequence KKPEDWD. These repeats reside in a highly hydrophilic region of the peptide, and are therefore likely to be exposed on the surface of the native antigen. As such, it is likely that this repeated region may represent one of the more highly immunogenic portions of the native antigen (J. A. Berzofsky, "Intrinsic and Extrinsic Factors in Protein Antigen Structure", *Science*, 229: 932–940, (1985)).

Several examples of such repeated sequences have been noted in other parasitic antigens, especially malaria (V. Enea, J. Ellis, F. Zavala, D. E. Arnot, A. Asavanich, A. Masuda, I. Quakyi and R. S. Nussenzweig, "DNA Cloning of *Plasmodium falciparum* Circumsporozoite Gene: Amino Acid Sequence of Repetitive Epitope", *Science*, 225:628–630, (1984); J. V. Ravetch, J. Kochan and M. Perkins, "Isolation of the Gene for a Glycophorin-Binding Protein Implicated in Erythrocyte Invasion by a Malaria Parasite", *Science*, 227: 1593–1597, (1985)), and *S. mansoni* (L. Bobek, D. M. Rekosh, H. van Keulen and P. T. LoVerde, "Characterization of a Female-Specific cDNA Derived from a Developmentally Regulated mRNA in the Human Blood Fluke *Shistosoma mansoni*", *Proc. Nat. Sci. USA*, 83:5544–5548 (1986)).

It appears that such repeated sequences may be a common feature of antigens isolated from many different parasitic species. In the case of other antigens which contain such repeated sequences, the repeated region often encodes the major epitope of the protein (W. R. Ballou, J. Rothbard, R. A. Wirtz, D. M. Gordon, J. S. Williams, R. W. Gore, I. Schneider, M. R. Hollingdale, R. L. Beaudoin, W. L. Maloy, L. H. Miller and W. T. Hockmeyer, "Immunogenicity of Synthetic Peptides from Circumsporozoite Protein of *Plasmodium falciparum*", *Science*, 228:996–999, (1985); W. E. Collins, R. F. Anders, M. Pappaioanou, G. H. Campbell, G. V. Brown, D. J. Kemp, R. L. Coppel, J. C. Skinner, P. M. Andrysiak, J. M. Favaloro, L. M. Corcoran, J. R. Broderson, G. F. Mitchell and C. C. Campbell, "Immunization of Aotus Monkeys with Recombinant Proteins of an Erythrocyte Surface Antigen of *Plasmodium falciparum*", *Nature* 323:259–262, (1986)). In order to discover if this is the case in λRAL-1, epitope mapping utilizing deleted versions of the λRAL-1 insert may be needed.

Applicants have taken a first step examining the role that the native antigen encoded by the mRNA that produced λRAL-1 may play in natural infections, showing that lysates containing the recombinant antigen stimulate the proliferation of PBMCs from a small number of infected individuals to a greater extent than does a control λgt11 lysate. This is important, since it is believed that the cellular immune system may be particularly important in the development of immunity against helminthic infections (R. B. Lal, T. J. Lynch and T. B. Nutman, "*Brugia malayi* Antigens Associated with Lymphocyte Activation in Filariasis", *J. Immunol.*, 139:1652–1657, (1987)). Although the responses seen to the recombinant lysate were both reproducible and significant, the overall response was not as impressive. However, previous studies have demonstrated that that the PBMCs of individuals infected with *O. volvulus* show both specific and non-specific supression of their response to antigens (J. I. Ngu, "Immunological Studies on Onchocerciasis", *Acta Trop.*, 35:269–279 (1978); B. M. Green, M. M. Fanning and J. J. Ellner, "Non-Specific Supression of Antigen-Induced Lymphocyte Blastogenesis in *Onchocerca volvulus* Infection in Man", *Clin. Exp. Immunol*, 52:259–265, (1983)).

A relatively low level of overall response seen to the recombinant lysate is therefore not surprising. It is possible that the non-specific supression induced by *O.*

*volvulus* infection may have been an asset in this case, by suppressing the strong response to *E. coli* antigens one would normally expect to see when using induced lysates as antigens in the blastogenesis assays. This may have allowed the response to the recombinant antigen to be demonstrated. In spite of this fact, it is quite likely that the response of patient cells relative to the control would be improved if purified preparations of the recombinant protein were used in place of crude extracts.

It will be possible to use purified preparations of recombinant antigens in animal model systems which mimic some of the pathological manifastations of human onchocerciasis (O. J. Donnelly, J. H. Rockey, A. E. Bianco and E. J. L. Soulsby, "Ocular Immunopathologic Findings of Experimental Onchocerciasis", *Arch. Ophthamol,* 102:628–634, (1984); J. J. Donnelly, H. R. Taylor, E. Young, M. Khatami, J. B. Lok and J. H. Rockey, "Experimental Ocular Onchocerciasis in Cynomolgus Monkeys:, *Inv. Ophthmol. and Vis. Sci.,* 27:492–499, (1986)), as well as models for protection against infection with the parasite (B. M. Greene, "Primate Model for Onchocerciasis Research. in Filariasis, Ciba Foundation Symposium #127", D. Evered and S. Clark, editors, John Wiley and Sons, New York, pp 236–240, (1987)).

The isolation of λRAL-1 and other clones which express antigens of *O. volvulus* infective larvae will therefore make it possible to examine the role that the antigens of infective larvae may play in development of immunity against onchocerciasis.

The present invention also encompasses an *O. volvulus* vaccine which comprises a recombinant *O. volvulus* antigen as described herein or an *O. volvulus* peptide sequence as described herein, or an immunogenic fragment thereof, e.g., the repeated region of the peptide, with or without an adjuvant, such as, for example, aluminum hydroxide or others.

The active component of the vaccine can be employed with a physiologically acceptable dilutent (medium), e.g., phosphate buffered saline. Generally speaking, the antigen or peptide concentration in a physiologically acceptable medium will be between approximately less than 1 milligram and more than 10 micorgrams per does.

The vaccine can be administered to a patient by any convenient route, e.g., by subcutaneous, intradermal or intramuscular injection. While the preferred route would depend upon the particular vaccine, it is believed that intramuscular injection will be generally suitable. Frequency of administration will vary depending upon the vaccine.

The invention will now be described with reference to the following non-limiting examples.

EXAMPLES

Example 1

Isolation of *O. volvulus* RNA and DNA

RNA was prepared from freshly excised nodules obtained from people infected with *O. volvulus* residing in Grand Bassa county, Liberia. The nodules were carefully trimmed to remove as much host tissue as possible. The parasite material was immediately homogenized in a solution of 6M guanidium thiocyanate, 5mM sodium citrate (pH 7.0), 100mM beta-mercaptoethanol and 0.5% sarkosyl, using a mechanical tissue grinder. The extracts were frozen at −20° C., and transported to the United States where RNA was isolated by centrifugation through a CsCl cushion, as described by V. Glisin, R. Crkvenjakov and C. Byus "Ribonucleic Acid Isolated by Cesium Chloride Centrifugation", *Biochemistry*, 13:2633–2637 (1974). Between 15 and 30 μg of RNA was obtained per adult female worm.

*O. volvulus* genomic DNA was prepared from adult worms that were freed from surrounding host tissue using the collagenase digestion protocol described by Schulz-Key. (H. Schulz-Key, E. J. Albiez and D. W. Buttner, "Isolation of Living Adult *Onchocerca volvulus* from Nodules", *Tropmed. Parasitol.*, 28:428–430 (1977)) and stored in liquid nitrogen. The DNA was prepared using the method described by Shah et al, (J. S. Shah, M. Karam, W. F. Piessens and D. F. Wirth, "Characterization of an Onchocerca-Specific DNA Clone from *Onchocerca volvulus*", *Am. J. Trop. Med. Hyg.*, 37: 376–384, (1987)). Between 3 and 10 μg of DNA was obtained per adult female worm. Each parasite DNA preparation was tested for the presence of containing host cell DNA by hybridization with a variety of probes for different human repeated genes. No contaminating host cell DNA was detected in any of the preparations used in the examples described below.

Example 2

In vitro Translation of Parasite RNA and Immunoprecipitation of the Translated Polypeptides Total RNA isolated from adult *O. volvulus* and *D. immitis* was translated in vitro in rabbit reticulocyte lysates (Promega Biotech, Madison, Wis.), using the protocol provided by the manufacturer. Rabbit antisera were prepared for use in immunoprecipitation of the translation products by heating to 60° C. for 20 minutes. Immunogobulins were precipitated by addition of ammonium sulfate to a final saturation of 40%. Precipitated protein was resuspended in 25mM Tris-HCl (pH 7.5), 100 mM NaCl, and dialyzed against the same buffer overnight at 4° C. Aliquots of the in vitro translation products and the purified antisera were mixed together and incubated overnight at 4° C. The antibody-antigen complexes were then bound to Protein A sepharose beads (Pharmacia, Uppsala, Sweden). The beads were washed repeatedly in a solution of 50 mM Tris (pH 6.9), 150 mM NaCl, 5 mM EDTA, 1% Nonidet P-40, 1% sodium deoxycholate, 0.2% sodium dodecyl sulfate (SDS), and 0.5% bovine serum albumin. The beads were resuspended in a solution of 62.5 mM Tris-glycine (pH 6.8), 3% SDS, 0.5% 2-mercaptoethanol and 10% glycerol, and heated for three minutes at 100° C. Freed polypeptides were separated on a 10% polyacrylamide gel, prepared as described by Laemmli (U. K. Laemmli, "Cleavage of Structural Proteins During the Assembly of the Head of Bacteriophage T4", *Nature*, 227:680–685 (1970).

Following electrophoresis, the gel was treated with the autoradiography enhancer Enlightening (New England Nuclear), dried and subjected to autoradiography.

Example 3

Preparation of O. volvulus Expression cDNA Library

*O. volvulus* RNA, prepared as described above in Example 1, was passed over an oligo-dT cellulose column, and poly A+ RNA was eluted from the column as described by Maniatis et al. (T. Maniatis, E. F. Fritsch and J. Sambrook, "Molecular Cloning: A Laboratory Manual", Cold Spring Harbor Laboratory, Cold Spring Harbor, N.Y. (1982)).

The poly A+ fraction from the column was then used to prepare first and second strand cDNA, using the RNAse H protocol of V. Gubler and B. J. Hoffman, "A Simple and Very Efficient Method for Generating cDNA Libraries", *Gene*, 25:263-269, (1982).

The cDNA was treated with EcoRI methylase (New England Biolabs, Beverly Mass.), using the conditions described by the manufacturer. Following methylation, synthetic EcoRI linkers (Collaborative Research, Lexington, MA.), phosphorylated as described by the manufacturer, were ligated to the ends of the cDNA. The preparation was then digested with EcoRI, and the freed linkers removed by chromatography on Bio Gel P-30 (Bio Rad Laboratories, Richmond, Calif.). The cDNA was then ligated to λgt11 arms (Stratagene, San Diego, Calif.). The resulting concatemers were packaged using Gigapack packaging extracts (Stratagene), using the protocol provided by the manufacturer. The library produced in this manner contained approximately 500,000 independent recombinant clones.

Example 4

Preparation of *O. volvulus* Antisera

To prepare antisera against *O. volvulus* infective larvae, living L3s were isolated by dissection from experimentally infected flies which had been maintained as described by Ham and Banya (P. J. Ham and A. J. Banya, "The Effect of Experimental Onchocerca Infections on the Fecundity and Oviposition of Laboratory Reared Simulium sp. (Diptera: Simuliidae)", *Tropenmed. und Parasitol.*, 35:61-66, (1984)).

A total of 164 living larvae suspended in RPMI tissue culture medium without adjuvant, were injected subcutaneously into a New Zealand white rabbit. At one week intervals following the first innoculation, the rabbit received two booster injections of approximately 100 living larvae. A final boost of 229 living infective larvae was administered five weeks after the initial innoculation. Eight weeks after the final injection of infective larvae, the rabbit was subjected to a detailed post-mortem examination. No evidence of developing parasites was found.

Antiserum against adult *O. volvulus* was prepared by homogenizing collagenase freed adult parasites in sterile saline in a Ten-Broeck glass-glass homogenizer. The extract was mixed 1:1 (v/v) with Freund's complete adjuvant, and used to immunize a New Zealand white rabbit. Following the initial immunization, the rabbit was boosted twice at weekly intervals with the same antigen-adjuvant mixture.

Example 5

Antibody Screening of the cDNA Library

Portions of the cDNA library (see Example 3) were plated at a density of approximately 35,000 plaque forming units per 135 mm petri dish, and the plaques induced to produce fusion proteins according to the protocol of Huynh et al, (T. V. Huynh, R. A. Young and R. W. Davis, "Constructing and Screening cDNA Libraries in λgt10 and λgt11, *Cloning Techniques: A Practical Approach*, D. Glover, editor, IRL Press, Oxford, (1984)).

Duplicate filters prepared from each plate were incubated overnight at room temperature with the appropriate antiserum. Antisera used in the screening procedure were diluted 1/20 in a solution of 20 mM Tris-HCl (pH 7.5), 0.5M NaCl, and 3% BSA (TBS/BSA). Antibodies reacting with *E. coli* antigens were removed prior to use by the protocol of Huynh et al, supra. Following incubation with the primary antiserum, the filters were washed in TBS/BSA, and exposed to Protein-A conjugated to horseradish peroxidase (Bio Rad Laboratories, Richmond, Calif.) for two hours at room temperature. Positive signals were identified by development in a solution containing 66 mM Tris-HCl, 20% methanol, 0.06% 4-chloro-1-napthol, and 0.02% hydrogen peroxide.

Example 6

Lymphocyte Blastogenesis Assays

Peripheral blood mononuclear cells (PBMCs) were isolated by Ficoll-Hypaque gradient centrifugation of fresh heparinized blood, obtained from *O. volvulus* infected individuals living in Liberia. The cells were suspended in a solution containing 40% RPMI 1640 tissue culture medium, 40% dimethylsulfoxide (DMSO), and 20% heat inactivated fetal calf serum, and frozen in liquid nitrogen. For the blastogenesis assays, the cells were thawed, washed twice in RPMI 1640 tissue culture medium and resuspended in RPMI 1640 containing 2mM L-glutamine, 100 U/ml penicillin, 100 U/ml streptomycin, and 10% heat inactivated pooled human serum. The cells were than plated at a concentration of $10^6$ cells/ml together with extracts of induced lysogen cultures of λRAL-1. Extracts were prepared as described by Huynh et al (supra), dialyzed against phosphate buffered saline, and filtered through a 0.45 μm filter before use. Extracts were used in a final concentration of 15 μg/ml of protein. Cultures were incubated for 78 hours at 37° C. in an atmosphere containing 5% $CO_2$. At this point, 1 μCi of $^3H$ thymidine (Amersham, Arlington Heights, Ill.) was added to the cultures, and the incubation continued for an additional 18 hours. Cells were harvested on filter paper, and $^3H$ thymidine incorporation assessed by counting the samples in a liquid scintillation counter. Results were expressed as the mean counts per minute of four culture wells ± the standard error of the mean.

Example 7

Affinity Purification of Antibodies Reactive with the Recombinant Antigen Produced by λRAL-1

Lysates of induced lysogen cultures of λgt11 and λRAL-1 were prepared according to the protocol of Huynh et al, supra. Protein from these lysates was coupled to cyanogen bromide activated Sepharose CL-68 (Pharmacia, Uppsala, Sweden), using the protocol provided by the manufacturer. An aliquot of the antiserum raised against adult *O. volvulus* was diluted 1/20 in TBS/BSA. The antibody solution was then preabsorbed to remove antibodies which reacted with *E. coli* antigens following the protocol of Huynh et al, supra. The antiserum preparation was then passed through a column containing the gel to which the λgt11 protein had been bound. The eluate was collected from this column, and passed over a column containing the gel to which the λRAL-1 lysate protein had been attached. Both columns were washed with a solution of 50mM Tris-HCl (pH 7.5). 0.5M NaCl and bound antibodies were eluted with a solution containing 0.2 M Tris (pH 7.5) and 8M urea. The eluate was adjusted to 3% (w/v) BSA and was dialyzed against TBS.

Example 8

DNA Sequencing

Isolated cDNA insert was subcloned into the plasmid vector pUC 13, and clones containing the inserted DNA in opposite orientations were identified. Plasmids containing the inserted DNA in opposite orientations were linearized by digestion with the restriction enzyme HindIII, and nested deletions were prepared using the exonuclease Bal 31. The deleted insert DNA was liberated by digestion with EcoRI and purified from an agarose gel as described by Vogelstein and Gillespie (B. Vogelstein and D. Gillespie, "Preparative and Analytical Purification of DNA and Agarose", *Proc. Nat. Acad. Sci. USA*, 76:615-619, (1979)).

The purified deleted insert DNA was then directionally cloned into the singal stranded bacteriophage vector M13 Mp18. Clones containing deletions whose ends differed by approximately 200 bp in length were isolated, and single stranded phage DNA prepared as described by Schreier and Cortese (P. H. Schreier and R. Cortese, "A Fast and Simple Method for Sequencing DNA Cloned in the Single-Stranded Bacteriophage M13", *J. Mol. Biol.*, 129:169-172. (1979)). This DNA was then sequenced using the dideoxynucleotide termination method (F. Sanger, S. Nicklen and A. R. Coulson, "DNA Sequencing with Chain Terminating Inhibitors", *Proc. Nat. Acad, Sci. USA*, 74:5463-5467, (1977)).

Example 9

Immunoprecipitation of in Vitro Translation Products of O. volvulus RNA

Figure 1:
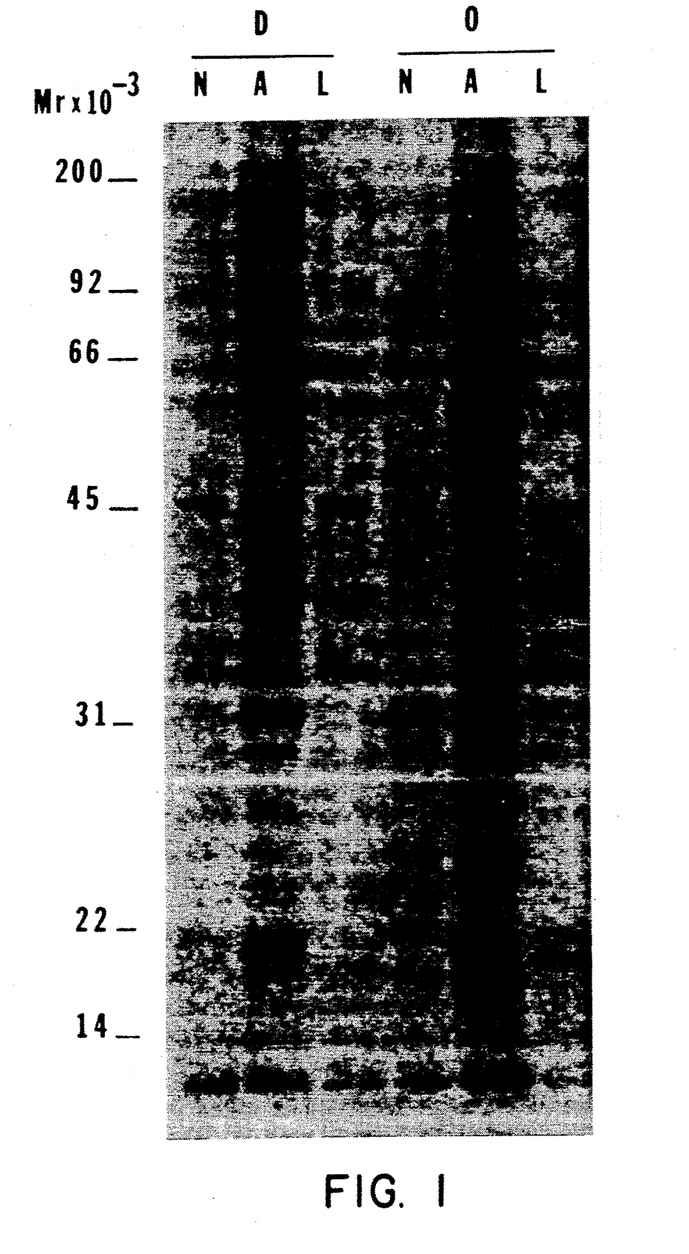
FIG. 1 is a photograph of the results of an immunoprecipitation of in vitro translation products of *O. volvulus* RNA.

In order to examine the ability of the antisera raised against the adult and larval stages of *O. volvulus* to recognize protein epitopes, adult RNA from both *O. volvulus* and *D. immitis* was translated in vitro. In both cases, this procedure resulted in the production of more than 100 polypeptides, the largest of which had an apparent size of greater than 100,000 daltons. These polypeptides were then immunoprecipitated with antisera raised against the adult and larval stages of *O. volvulus*. The results of this example are shown in FIG. 1. The antiserum raised against the adult form of the parasite recognized greater than twenty different sized polypeptides (lane A, set O in FIG. 1). For most of these polypeptides, polypeptides of similar molecular weight were also recognized in the in vitro translation products of *D. immitis* (compare the lanes labelled A in FIG. 1). Some of the polypeptides recognized by the adult antiserum did appear to be specific for *O. volvulus*, however. The most prominent of these was a polypeptide of approximately 20,000 daltons (lane A, set O of FIG. 1).

In contrast to the antiserum raised against the adult form of the parasite, the antiserum raised against the larval form recognized only six different polypeptides (lane L, set O of FIG. 1). These polypeptides were a subset of those recognized by the adult antiserum (compare lanes A and L, set O of FIG. 1). These results demonstrated that both the antiserum against both the adult and larval forms of the parasite were capable of recognizing protein epitopes present in the absence of any polysaccaharide moieties.

Example 10

Isolation of cDNA Clones Expressing Epitopes Found in *O. volvulus* Infective Larvae In order to identify clones expressing epitopes found in infective larvae, a portion of the cDNA library described hereinabove in Example 3, representing approximately 200,000 independent recombinant clones, was screened with the larval antiserum. From this initial screen, six clones were purified which reacted reproducibly with the larval antiserum. When the inserted cDNA in each of these clones was tested for their ability to hybridize to the inserted cDNA in the other clones, it was determined that these clones could be divided into two classes.

Aliquots of plate lysates of plaque purified immunoreactive clones were spotted in a grid pattern on a lawn of *E. coli* strain Y1090.

Figure 2:
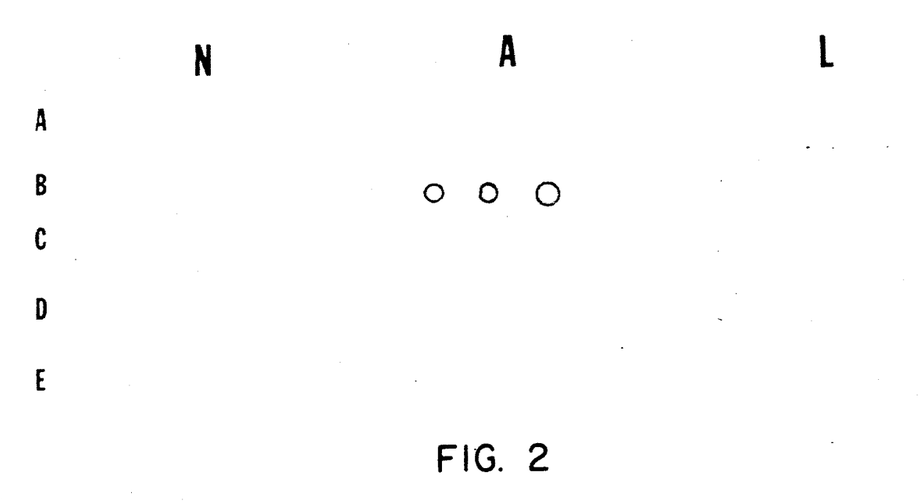
FIG. 2 is a photograph depicting the identification of cDNA clones expressing antigens recognized by rabbit antisera raised against *O. volvulus.*

Plaque lifts were prepared from representatives from each of these classes, and the filters probed with the larval and adult antisera. As shown in FIG. 2, rows C through E, all of the clones which reacted with the larval antiserum also reacted with the adult antiserum. However, it was possible to isolate clones with the adult antiserum that did not react with the larval antiserum (FIG. 2, row B). A member of the class of clones that reacted the most strongly with the larval antiserum (FIG. 2, rows C and D), designated λRAL-1, was chosen for further analysis.

Example 11

Induction of Lymphocyte Blastogenesis in Cells from O. volvulus Infected Individuals by Induced Lysogen Cultures of λRAL-1

As a first step towards examining if the native protein related to the recombinant antigen produced by λRAL-1 plays any role in the development of an immune response against the parasite in natural infections, the ability of lysates containing the recombinant antigen to stimulate proliferation of peripheral blood mononuclear cells (PBMCs) isolated from infected individuals was examined. As shown in Table 1 hereinbelow lysates containing the recombinant protein stimulated proliferation of PBMCs from three infected individuals to a greater extent than did control lysates. The difference in the level of stimulation between the control and recombinant lysates was significant, as judged by Student's paired t-test ($p<0.01$). In contrast, when PBMCs from uninfected individuals residing in the same area were used in the assay, no significant difference between the two lysate preparations was seen (Table 1).

To generate the data for Table 1, blastogenesis assays were preformed on PBMCs isolated from three patients with *O. volvulus* infections, as well as cells from three control individuals residing in the same area. The control individuals were free of clinical symptoms of onchocerciasis, contained no detectable skin microfilariae, and did not have an antibody response to *O. volvulus*, as judged by Western blot analysis with crude *O. volvulus* adult worm antigen preparations. Results are expressed in Table 1 as the mean counts per minute of four independent determinations ± the standard error of the mean.

TABLE 1

| Cell Source | Culture Additions | | |
| --- | --- | --- | --- |
| | Buffer | λgt 11 Lysate | λRAL-1 Lysate |
| Patients | | | |
| A | 379 ± 74 | 472 ± 60 | 1114 ± 322 |
| B | 296 ± 23 | 461 ± 10 | 878 ± 48 |
| C | 180 ± 10 | 543 ± 151 | 1165 ± 6 |
| Controls | | | |
| A | 317 ± 54 | 725 ± 187 | 799 ± 112 |
| B | 390 ± 42 | 404 ± 34 | 319 ± 46 |
| C | 425 ± 29 | 365 ± 65 | 421 ± 66 |

Example 12

Expression of the Inserted cDNA of RAL-1 in the Plasmid Vector PUC 13.

Figure 3:
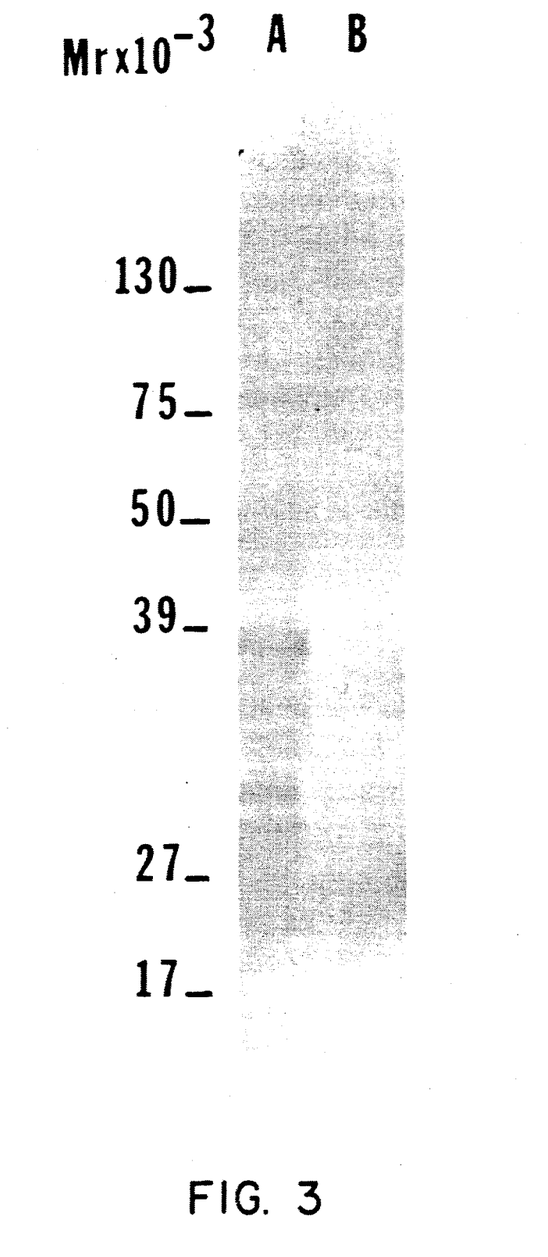
FIG. 3 is a photograph of a Western blot depicting the inserted DNA of λRAL-1,which encodes an antigen which an apparent molecular weight of 38,000 when inserted into plasmid vector pUC 13.

Initial experiments with extracts prepared from induced lysogen cultures of λRAL-1 suggested that the clone was not producing a stable recombinant polypeptide. However, when the inserted DNA was subcloned into the plasmid vector pUC 13 a stable product with an apparent molecular weight of 38,000 was produced (FIG. 3).

Cultures of *E. coli* containing pUC 13 plasmids into which the insert of λRAL-1 had been cloned in opposite orientations were induced by the addition of isopropyl beta-D-galactopyranoside to a final concentration of 10mM. Crude lysates of the cultures were prepared, and used to prepare a Western blot, as described by Towbin et al, (H. Towbin, T. Staehelin and J. Gordon, "Electrophoretic Transfer of Proteins From Polyacrylamide Gels to Nitroceullulose Sheets: Procedure and Some Applications", *Proc. Nat. Acad. Sci. USA* 76 4350-4354, (1979)).

The blot was exposed to rabbit antiserum raised against *O. volvulus*, and developed with Protein-A conjugated with horseradish peroxidase.

A doublet of smaller products recognized by the antiserum was also produced from this preparation. The relative amount of these products varied from preparation to preparation, suggesting that the smaller polypeptides were degradation products of the larger polypeptide. As is shown in FIG. 3, the production of this polypeptide was dependent on the orientation in which the cDNA insert was cloned into the vector plasmid, suggesting that is production was being controlled by the beta-galactosidase gene of pUC 13.

Example 13

Identification of the Parasite Antigen Produced by the mRNA that Gave Rise to λRAL-1

To characterize the native antigen encoded by the mRNA that gave rise to λRAL-1, antibodies reacting with the recombinant protein were affinity purified as described in Example 7.

Adult *O. volvulus* were homogenized in a solution of 50mM Tris-HCl (pH 7.5), 1mM EDTA, 0.1%SDS, 2mM iodoacetamide, 2mM phenyl methyl sulphonyl fluoride, 2mM TLCK, 2mM TPCK and 2 µg/ml leupeptin. The homogenate was subjected to centrifugation at 81,000xg for one hour at 4° C. Aliquots of the supernatant containing 150 µg of protein were used to prepared a Western bolt as described by Towbin et al, supra. The blot was exposed to affinity purified antibodies, prepared as described in Example 7 and the blot developed with Protein A conjugated with horseradish peroxidase, as described hereinabove.

Figure 4:
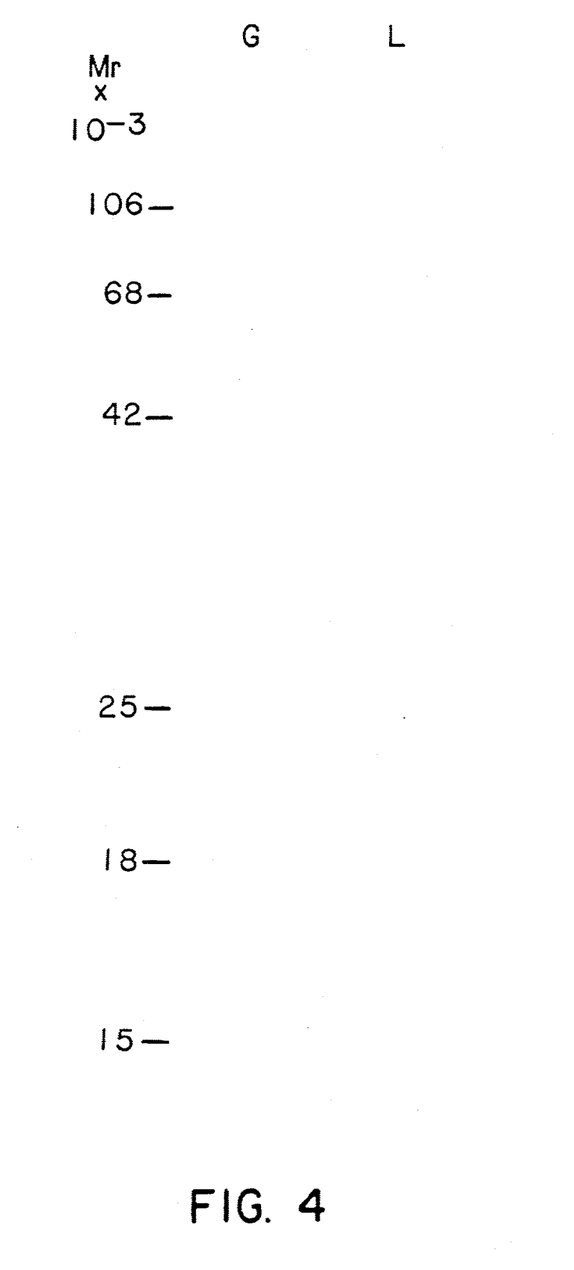
FIG. 4 is a photograph of a Western blot depicting the identification of native parasite antigen represented by λRAL-1 proteins.

These antibodies were used to probe Western blots of adult *O. volvulus* proteins. The affinity purified antibodies recognized a single band of an apparent molecular weight of 42,000 (FIG. 4, lane L). No proteins were recognized by antibodies affinity purified using immobilized proteins prepared from a control λgt11 lysate (FIG. 4, lane G).

Example 14

Organization and Expression of the Gene Corresponding to λRAL-1

To determine the size of the message that gave rise to λRAL-1, poly A+ RNA, prepared as described hereinabove was separated on denaturing agarose gels containing formaldehyde, and the RNA transferred to Gene Screen nylon membranes (New England Nuclear, Boston, Mass.) as described by the manufacturer. The resulting Northern blot was probed with purified insert from λRAL-1 which had been radioactively labelled by nick translation.

Figure 5:
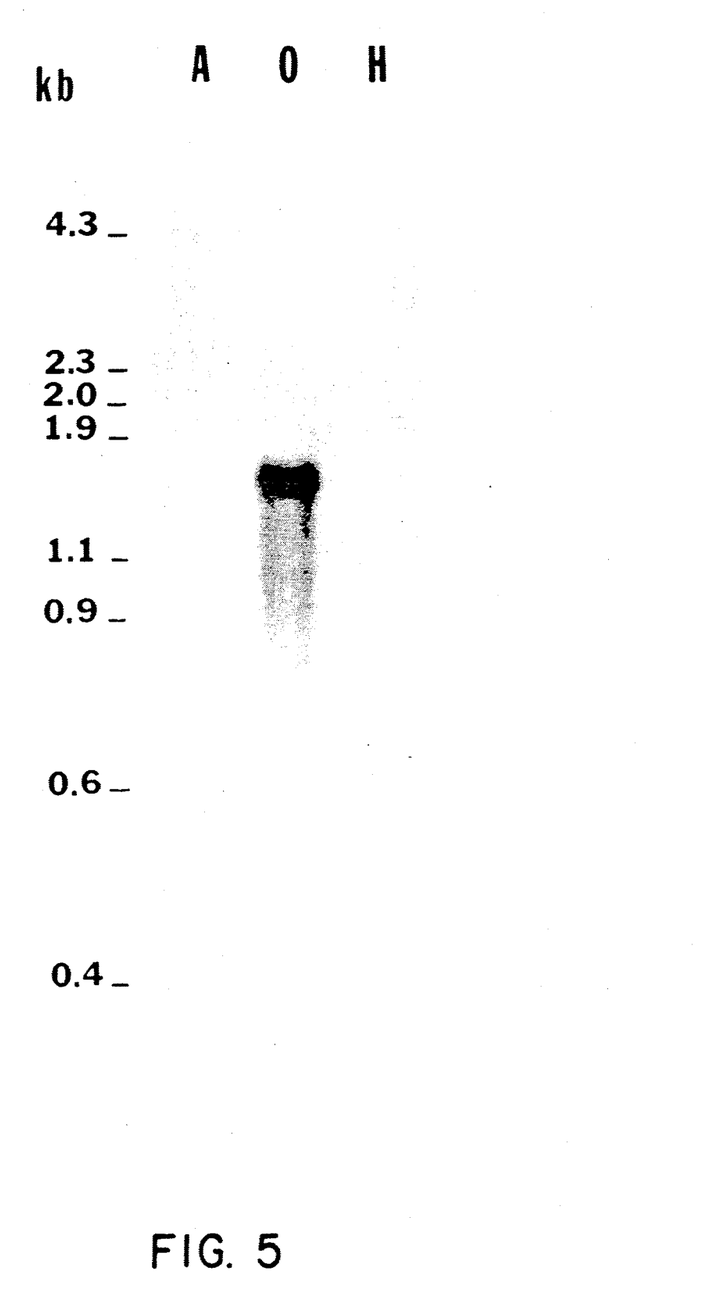
FIG. 5 is a photograph of a Northern blot analysis of Adult *O. volvulus* RNA Probed with the inserted DNA of λRAL-1. Lane A=*A. suum* RNA, Lane O=*O. volvulus* adult RNA, and Lane H=Human RNA.

As FIG. 5, lane O demonstrates, the inserted DNA from λRAL-1 hybridized to a single message of 1450 bases in size. No hybridization was detected to RNA isolated from uninfected human cells (FIG. 5, lane H). The results presented in FIG. 5 also suggest that an identical message is not present in mRNA prepared from the intestinal helminthic parasite *A. suum*. However, in overexposed autoradiographs of the blot, a small amount of hybridization to a band of 1650 bases is seen in *A. suum* RNA.

The radiolabelled insert from λRAL-1 was also used to probe a Southern blot prepared with both *O. volvulus* and uninfected human placental DNA. Two restriction enzymes which did not cut within the insert of λRAL-1 were used to prepare the blot.

Aliquots of human and *O. volvulus* genomic DNA digested with the restriction enzymes EcoRI and HindIII were used to prepare a Southern blot as described by Southern (E. H. Southern, "Detection of Specific Sequences Among DNA Fragments Separated by Gel Electrophoresis", *J. Mol. Biol.*, 98:503-517, (1975)).

The blot was probed with the purified insert from λRAL-1 that had been radioactively labelled by nick translation.

Figure 6:
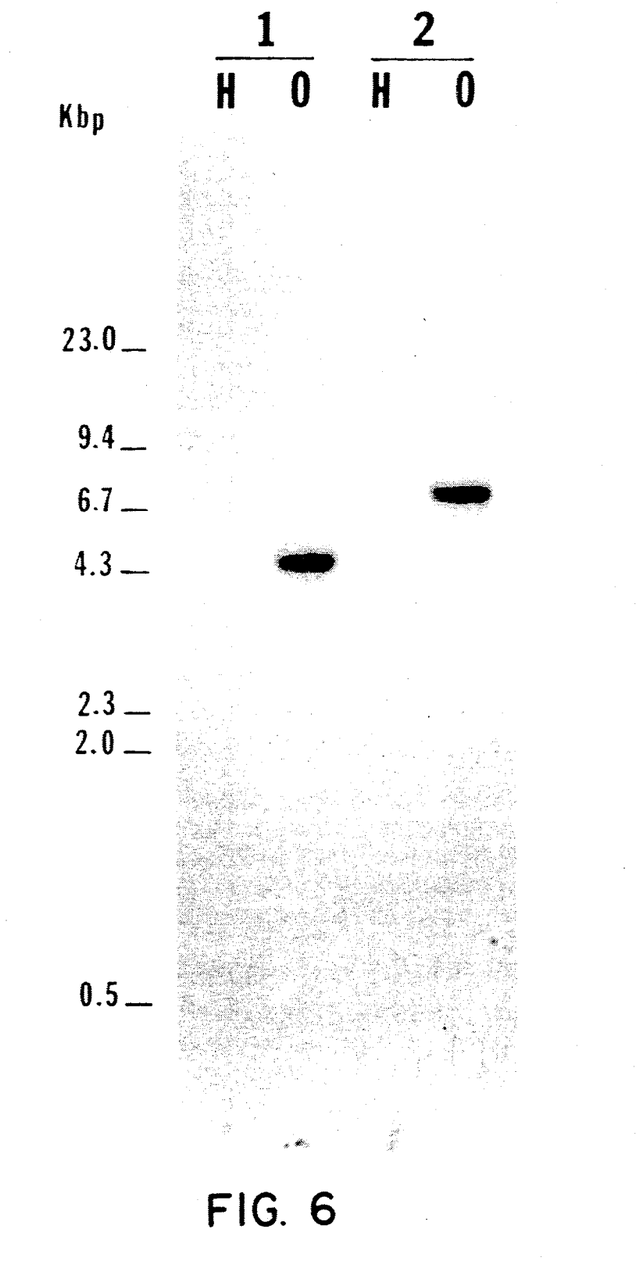
FIG. 6 is a photograph of a Southern blot analysis of Genomic DNA probed with the inserted DNA of λRAL-1.

As is shown in FIG. 6, the insert from λRAL-1 hybridized to a single band in *O. volvulus* genomic DNA which had been digested with either HindIII or EcoRI. No hybridization was detected to uninfected human genomic DNA, demonstrating that the clone λRAI-1 was of parasite origin.

Example 15

DNA Sequence Analysis of RAL-1

In order to determine if the inserted DNA of λRAL-1 was related to any previously described protein or nucleic acid sequence the DNA sequence of the inserted DNA was determined. The sequencing strategy and the complete DNA sequence of the inserted DNA is shown in FIG. 7. The insert of λRAL-1 was found to be 1076bp in length. Of these 1076bp, only 12bp appear to be derived from the poly A tract at the 3' end of the message. The sequence contains one large open reading frame, which extends from bases 1-1008. This open reading frame is in frame with beta-galactosidase gene of pUC 13. Overall, the predicted molecular weight of a putative fusion protein produced by this open reading frame was 41,454. Screening of the complete Genbank nucleic acid and NBRF protein data banks revealed no sequences which contained significant homologies to the inserted DNA of λRAL-1, or to the polypeptide predicted by the long open reading frame.

As is shown in FIG. 7, the long open reading frame enclosed a polypeptide which contained three repeats of the amino acid sequence KKPEDWD. The three repeats are separated from one another by two unrelated stretches of 10 amino acids each. Comparison of the DNA sequences of the repeats demonstrated that the exact homology of the repeats is not conserved at the nucleic acid level. Relative hydrophilicity plots using the algorithm of Hopp and Woods (T. P. Hopp and K. R. Woods, "Prediction of Protein Antigenic Determinants from Amino Acid Sequences", *Proc. Nat. Acad. Sci. USA*, 78:3824-3828, (1981)) indicated that the region containing the repeated sequence is highly hydrophilic.

Following the long open reading frame, the inserted cDNA contained a putative untranslated region of 56bp. As is shown in FIG. 7, this region contained two stretches of the poly A tract addition signal sequence AATAAA (M. Wickens and P. Stephenson, "Role of the Conserved AAUAAA Sequence: Four AAUAAA Point Mutants Prevent Messenger RNA 3' End Formation", *Science*, 226:1045-1051, (1984)) within 30 bases of the start of the poly A tract at the 3' end of the message.

It will be appreciated that the instant specification and claims are set forth by way of illustration and not limitation, and that various modifications and changes may be made without departing from the spirit and scope of the present invention.

What is claimed is:

1. An isolated and purified nucleic acid having the nucleotide sequence according to FIG. 7.

2. A recombinant vector comprising the nucleotide sequence of claim 1.

3. A host cell transformed with the recombinant vector of claim 2.

4. An isolated and purified cDNA clone which comprises the DNA sequence shown in FIG. 7 and which encodes a protein with an apparent molecular weight of 42,000.

5. An *E. coli* host cell transformed with the cDNA sequence according to claim 4 which is identified as ATCC No. 67737.

6. An isolated and purified DNA sequence which codes for an *O. volvulus* peptide sequence, said peptide containing three repeats of the polypeptide sequence KKPEDWD.

7. A replicative recombinant cloning vehicle comprising the DNA sequence according to claim 6.

8. A host cell transfected or transformed with the replicative recombinant cloning vehicle according to claim 7.

* * * * *